(12) United States Patent
Fuerll et al.

(10) Patent No.: US 7,650,794 B2
(45) Date of Patent: Jan. 26, 2010

(54) METHOD AND DEVICE FOR MEASUREMENT OF MECHANICAL COMPACTION OF AGRICULTURAL GOODS

(75) Inventors: Christian Fuerll, Potsdam (DE); Hartmut Schemel, Brueck (DE)

(73) Assignee: Leibniz-Institut fuer Agrartechnik Potsdam-Bornim E. V., Potsdam (DE)

( * ) Notice: Subject to any disclaimer, the term of this patent is extended or adjusted under 35 U.S.C. 154(b) by 134 days.

(21) Appl. No.: 11/635,402

(22) Filed: Dec. 7, 2006

(65) Prior Publication Data

US 2007/0151467 A1    Jul. 5, 2007

(30) Foreign Application Priority Data

Dec. 7, 2005    (EP)    .................................. 05090334

(51) Int. Cl.
*G01N 9/36*    (2006.01)
(52) U.S. Cl. ........................................................ 73/818
(58) Field of Classification Search .................... 73/818
See application file for complete search history.

(56) References Cited

U.S. PATENT DOCUMENTS

| | | | | |
|---|---|---|---|---|
| 4,034,543 | A * | 7/1977 | Voth et al. ..................... 56/341 |
| 6,155,103 | A * | 12/2000 | Diekhans et al. ............... 73/73 |
| 6,327,899 | B1 * | 12/2001 | Diekhans et al. ............... 73/73 |
| 6,669,557 | B2 * | 12/2003 | Adams et al. .................. 460/7 |
| 7,077,743 | B2 * | 7/2006 | Quincke et al. ................. 460/7 |
| 7,231,814 | B2 * | 6/2007 | Platon et al. .................... 73/73 |
| 7,302,837 | B2 * | 12/2007 | Wendte ..................... 73/146.5 |
| 2004/0200200 | A1 * | 10/2004 | Quincke et al. ........... 56/10.2 R |

FOREIGN PATENT DOCUMENTS

| | | |
|---|---|---|
| DE | 10236515 C1 | 9/2003 |
| DE | 10306725 A1 | 9/2004 |
| EP | 0843959 A1 | 5/1998 |

* cited by examiner

*Primary Examiner*—Lisa M Caputo
*Assistant Examiner*—Freddie Kirkland, III
(74) *Attorney, Agent, or Firm*—Kriegsman & Kriegsman

(57) ABSTRACT

A process and a device for measuring the mechanical compaction in the depth of an agricultural material, wherein measurement is made with a density sensor of the density of the agricultural material continuously or discontinuously online during the ongoing compacting of an agricultural material.

22 Claims, 5 Drawing Sheets

METHOD AND DEVICE FOR MEASUREMENT OF MECHANICAL COMPACTION OF AGRICULTURAL GOODS

BACKGROUND OF THE INVENTION

The invention relates to a process and a device for measuring the mechanical compaction the depth of an agricultural material as well as a device for carrying out the process.

Agricultural materials, such as, for example, crushed grains of wheat or corn or chopped green materials, may be preserved by compacting and thus reducing the volume of trapped air. This process is employed on a large scale, for example, when chopped corn or grass is placed in horizontal silos for silage. Here, chopped green materials are introduced into a silo in layers and compacted by driving over them with a tractor, a wheeled loader, or a roller. The quality of the conserved fodder and the storage losses are crucially determined by the compacting and the achieving of a minimum storage density.

Employed primarily for research purposes are processes in which special measuring instruments are used to conduct measurements at discrete points and discontinuously. This is possible using radiometric probes, which are inserted at least 20 cm deep into the material. Used in practice are also coring cylinders, by means of which a defined volume of the material is withdrawn and weighed in order to calculate the density. Both processes are so tedious and associated with risks that, as a rule, a measurement of density is dispensed with. Instead, at best a visual evaluation is made on the basis of the penetration depth of the compacting vehicle, although this does not allow a quantitative conclusion.

Known are measuring devices on compacting rollers for creating construction subsurfaces in, for example, road construction, Used here is an acceleration sensor, which is joined to the vibrating roller of the machine. On a subsurface that is defined by a specific composition and has a compaction determined beforehand by measurement technology, the sensor delivers a reference signal, which then serves as set target for the entire area of the same subsurface. This reference value is indicated in various ways to the driver in the cabin of the compacting vehicle. The process has the drawback that the density is not measured directly. Moreover, it may be employed only for vibrating machines having a constant characteristic frequency.

Described in DE 102 36,515 and EP 0 843,959 are measuring devices for determining the constituent substances and/or characteristics of harvested material in an agricultural machine. However, a measurement of the compaction of a subsurface in its depth is not described.

Further described in DE 103 06,725 is a process and a device for determining the parameters of harvested materials by using a compacting device that can be filled with a sample of the harvested material during the working process. In the compacting device, a partial quantity separated from the flow of material is compacted to a specific value in order to rule out the influence of density on the material parameters to be measured. The measurement of the parameters of the harvested material is conducted in a compacting chamber intended for receiving the samples. Here, the creation of a constant density serves as a means of being able to quantify unequivocally other material parameters that depend on the density. The density here is determined from the chamber volume and the weight of the material contained in it and does not involve any detection by measurement technology of the density of a subsurface during traversal thereof.

SUMMARY OF THE INVENTION

The object of the present invention is the measurement of the mechanical compaction in the depth of an agricultural material in order to make possible an optimal conservation of the agricultural material.

The object of the invention is solved by a process in which a density sensor is used during the ongoing compacting of an agricultural material to measure the density of the agricultural material continuously or discontinuously online.

An agricultural material is understood to mean all types of agricultural materials, such as, for example, undried harvested wheat and kernels of corn, fodder, or chopped green materials.

An agricultural material that is stored in silos, in particular, horizontal silos, on open surfaces, or in halls, is compacted for conservation. In this process, the agricultural material is introduced into the silo in layers. The agricultural material is compacted by driving over it with a compacting vehicle, such as, for example, a tractor, a roller, a wheeled loader, or another suitable vehicle. This compacting process reduces the volume of trapped air and thus conserves the material. The quality of the conserved material and the storage losses are crucially determined by the compacting and the achieving of a minimum storage density.

Only when the density during the compacting operation can be measured and displayed is it possible for the driver/operator of a compacting apparatus to achieve the required storage density with a minimum of effort or expenditure.

The measurement data of the density sensor are preferably conveyed to an evaluating unit and displayed on a display unit. The density of the agricultural material is measured online; that is, at the same time as the compacting of the agricultural material, the values recorded by the measuring sensors are conveyed to the evaluating unit and from there to the display unit. Thus, during the compacting, the user of a compacting apparatus receives current information on the density of the agricultural material that he is just then compacting. This makes it possible for him, during the compacting, to decide whether the material requires further compacting.

The measurement is conducted here both continuously and discontinuously. In a continuous measurement, permanent measured values are recorded and conveyed to the evaluating unit. However, it is also possible, either through the design or the mode of attachment of the measuring sensor, to determine the measured values only at specific intervals. In discontinuous measurement, various measuring points are established at which a measurement is conducted. However, here, too, the acquired data are also conveyed to the evaluating unit at the same time as the measurement.

The density is preferably measured on the surface of the agricultural material. In this case, the density is measured down to a depth of approximately 30 cm. The density sensor is guided without contact over the surface, although it may also be brought into contact with the surface. The contactless measurement has the advantage that the measuring units are better protected against soiling or damage.

For each type of agricultural material, there is a specific density at which the material is optimally conserved. The agricultural material is further compacted until this density, that is, the desired specified value, is attained.

The compaction of the surface of the agricultural material is important. If the top layer of the material is compacted, it is more difficult for gases to escape from the lower layers of the agricultural material, by means of which an optimal conservation of the material is achieved. The lower layers of the material are compacted by the weight of the layers lying above them.

In a preferred embodiment of the invention, the values measured by the density sensor are compared with the specified value in the evaluating unit and the deviation between the values is conveyed to the display unit. This process enables the driver of a compacting vehicle or of another compacting apparatus to perform an online density measurement during compacting. Accordingly, at the same time as the agricultural material is traversed, he is informed of its nature and is thus capable of deciding whether the spot of the agricultural material that he is working requires further compacting.

However, the specified value of an agricultural material also depends on the moisture of the material. Therefore, another sensor is preferably used to measure the moisture of the agricultural material and the measured values of the moisture determination are conveyed to the evaluating unit. The moisture sensor may be integrated in the sensor for the density measurement or it may be an independent sensor. During the measurement, the moisture sensor may be brought into contact with the agricultural material. However, it is also possible for the moisture measurement to be conducted without any contact, that is, for the moisture sensor to be guided above the surface of the agricultural material without any contact during the measurement.

In another preferred embodiment of the invention, the measured value of the agricultural material is compared with the specified value in the evaluating unit, taking into consideration the moisture of the agricultural material and the deviation is conveyed to the display unit.

Preferably, the position at which a measured value is taken is determined and the value of this position is conveyed to the evaluating unit. By not measuring the density alone, but rather, simultaneously, determining the position at which the density determination has taken place, it is possible to map the surface of the agricultural material. In this way, the user is afforded an overview of the entire agricultural material to be compacted. Furthermore, the locations that require further compacting are displayed for him.

The display unit preferably indicates the density of the agricultural material acoustically and/or depicts it visually. The display unit thus represents an interface between the evaluating unit and the user. It makes it possible for him to review the acquired data. An overview is presented to the user, from which he can infer all of the data that are important to him relative to the position, the density of the agricultural material, the moisture of the agricultural material, and the optimal compaction for this agricultural material. These data may be processed by appropriate software in a user-friendly manner. This can be made in the form of individual values, tables, diagrams, or the like. However, it is also possible for the user to display an overview map of the surface of the agricultural material in a silo, in which the compaction of the material is depicted by way of special colors assigned to the individual density values.

However, the measured values may also be indicated in acoustic form, for example, by a signal that sounds when the requisite density is attained.

Furthermore, the object of the invention is solved by a device that consists of at least one measuring sensor and at least one display unit, which are connected to an evaluating unit. During compacting of the agricultural material, the measuring sensor delivers measured values, which are conveyed to the evaluating unit. In the evaluating unit, the measured values are processed, that is, evaluated by software. Thus, in the evaluating unit, the measured values may be compared with specified values, such as, for example, the optimal density for conservation. These processed data are then conveyed to the display unit.

Here, the transmission of the measured values may be accomplished by way of a direct connection via a cable or else by way of a wireless connection, such as, for example, a radio link or the like.

The evaluating unit may be integrated into the measuring sensor or into the display unit or may exist as a separate assembly.

The evaluating unit may be provided with a data memory, which stores the measured data and compares them with the values of further measurements.

The measuring sensor is preferably a density sensor and/or a moisture sensor. The density senor may be a radiometric probe. However, it is also possible to use any other density sensor that makes possible a measurement of the density of the agricultural material to be made at the same time as the compacting process.

In a preferred embodiment of the invention, the measuring sensor is attached to a plate. The attachment of the measuring sensor to a plate has the advantage that the surface on which the measuring sensor is applied on the agricultural material is enlarged and a sinking of the measuring sensor into soft material can be prevented.

The density measurement of the agricultural material may be impaired by the level of moisture of the material. Therefore, a second measuring sensor advantageously measures the moisture of the agricultural material.

The density sensor and/or the moisture sensor are fastened to the compacting apparatus in such a way that they measure, at the same time as the compacting during traversal of the agricultural material, for example, its density or its moisture, respectively. The values measured in this way are conveyed to the evaluating unit and from there to the display unit. In this way, the user of the compacting apparatus is informed during the compacting whether further compacting is required.

The density sensor and/or the moisture sensor are fastened to the compacting apparatus in such a way that they are brought into contact with the surface of the agricultural material; however, it is also possible to guide the sensors over the surface of the material without any contact during the measurement.

The density sensor and the moisture sensor may be present as a multifunctional measuring sensor.

Furthermore, it is possible to measure additional parameters, such as, for example, the temperature or the air pressure. To this end, additional measuring sensors may be connected to the evaluating unit.

In a preferred embodiment of the invention, a measuring unit for determining the position of the measurement is provided. This has the advantage that it is possible to determine which locations of the surface have already been compacted and which have not.

Also of advantage is to make the measuring unit a navigation system, which determines the position of the measurement and conveys it to the evaluating unit. The evaluating unit can then use the positional data to calculate which locations of the agricultural material have already been sufficiently compacted and which locations still require additional compacting.

The measuring unit is preferably a path measurement system, a distance measurement system, or a position measurement system.

Preferably, two or more of the measuring systems mentioned are provided.

The values measured by the measuring sensors and/or the measuring units and compared with the specified value of the agricultural material by the evaluating unit are preferably displayable acoustically or visually by a display unit. On the basis of the values obtained by the measurement of density, moisture, and position, a mapping of the entire surface of the agricultural material is possible. The data acquired in this way can be presented on the display unit and afford information on which regions of the agricultural material have to be compacted and which already correspond to the desired density.

The density measuring device is preferably installed in or attached to a compacting apparatus. A compacting vehicle may already be equipped with such a density measuring device, for which a density sensor is situated on the underside of the vehicle.

However, parts of the device may also be arranged in a stationary measuring station. This measuring station then exists in radio contact with the compacting vehicle.

The measurement may also be performed by another vehicle. In another embodiment of the invention, the device is fastened to a separate measuring vehicle. In this embodiment, the measuring vehicle drives over the surface of the agricultural material to be compacted and collects measurement data on the nature of the material. The data collected in this way are conveyed online to the evaluating unit and supplied to the user via the evaluating unit. Here, the display unit is situated in or on the compacting apparatus, whereas the evaluating unit may be introduced on both the compacting apparatus and the measuring vehicle.

The process for measuring the compaction of agricultural material and the associated density measuring device allow the density of the agricultural material to be measured online during the compacting operation. The process and the density measuring device can consequently also be used in other fields in which a density measurement is required during the compacting.

The device or parts of the device are preferably arranged on a runner. The runner can be hitched onto a compacting vehicle and makes it possible for the measuring sensor to be guided over the agricultural material to be compacted or already compacted material.

Here, the runner is joined to the compacting apparatus by means of a linear guide in such a way that the runner is dragged along, but can move with respect to the hitch to the apparatus in such a way that it is adapted to the surface of the material.

BRIEF DESCRIPTION OF THE DRAWINGS

The invention will be explained in more detail below on the basis of drawings.

These show, in detail.

DETAILED DESCRIPTION OF THE INVENTION

Figure 1:
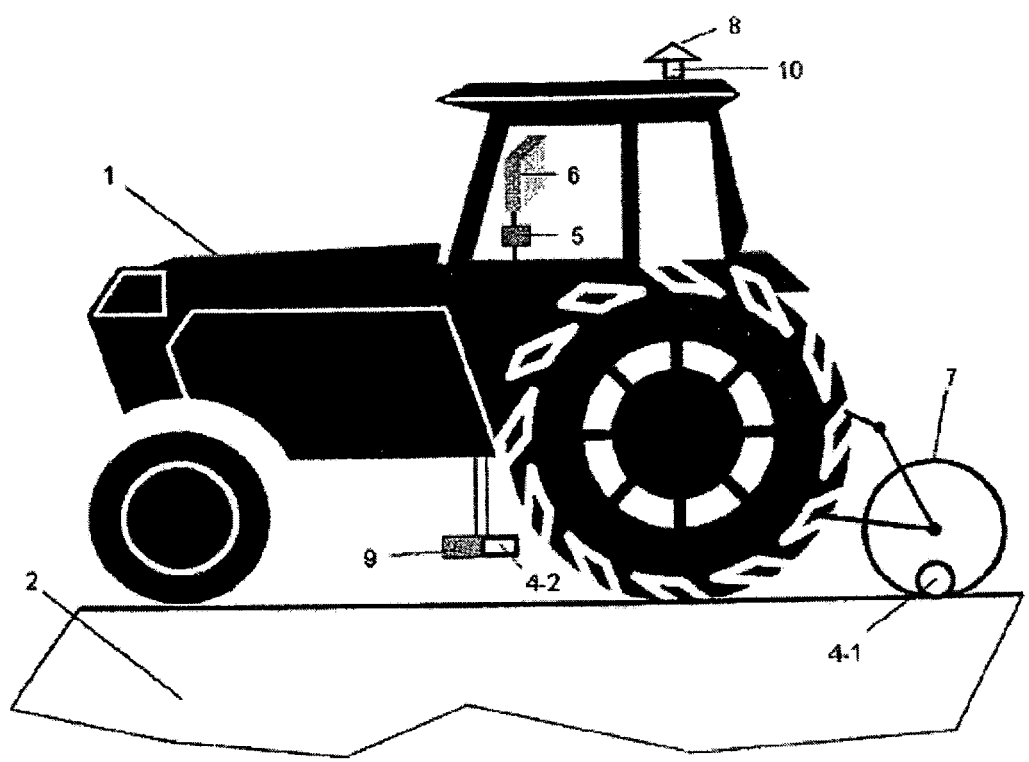
FIG. 1 a tractor for compacting with a device for measuring the density.

FIG. 1 shows a compacting apparatus 1, such as, for example, a tractor, which is employed for compacting an agricultural material 2, such as, for example, a stock of fodder. Installed in this tractor is a device 3 (see FIG. 2) for measuring density, which consists of a density sensor 4, an evaluating unit 5, and a display unit 6. The evaluating unit 5 may be integrated into the density sensor 4 as well as into the display unit 6. However, it is also possible for the evaluating unit 5 to be an independent instrument, which is connected between the density sensor 4 and the display unit 6.

For purposes of illustration, the tractor is depicted with two density sensors 4-1 and 4-2.

If a density sensor 4-1 is used, whose functional principle requires contact with the measured material, then it is appropriately installed in a measuring wheel 7. In this case, the contact and measuring surface of the density sensor 4-1 is fitted into the running surface of the measuring wheel 7. The measuring wheel 7 is fastened to the tractor in a floating manner, so that it can adapt to the unevenness of the surface of the agricultural material 2, and the density sensor 4-1 is pressed onto the material 2 by the constant force of the dead weight of the measuring wheel 7. If no measurement is to be conducted, it is possible to lift the measuring wheel 7 by using the tractor's hydraulic system. The measuring wheel 7 can be installed in front of, behind, or between the axels of the tractor. It may also be connected to a special lifting device if a standard hydraulic system is not available at the desired place of installation.

In the example depicted, because the density sensor 4-1 rotates together with the measuring wheel 7, a measured quantity can always only be obtained at intervals of the wheel circumference, unless several density sensors 4-1 are arranged around the circumference.

Also conceivable is the installation of the density sensor 4-1 in a runner or sled, which is dragged over the agricultural material 2 or is guided actively along the surface by means of a special hitch. Through suitable measures, however, it can be assured, then, that the runner or sled does not dig into the agricultural material 2 or push the material 2 in front of it.

The density sensor 4-1 is supplied with electrical power via a suitable power transformer, such as, for example, a slip ring, from the power system of the tractor. The measured values are transmitted directly or by radio to an evaluating unit 5 with a display unit 6 (e.g. a display or a monitor) in the tractor cabin. The measured density can be displayed in digital or analog form—for example, in a color scale. Usually, the density is displayed at the location at which the measuring wheel 8 is just situated and the measurement is being made. However, it is also possible to receive a navigation signal (e.g., GPS) via the antenna 8 of a navigation system 10, to link it to the density signal in the evaluating unit 5, and thus to depict the density value over the silo cross section. For determination of position, it is also possible to use a signal that is delivered by a known distance sensor on the tractor or by the tractor's electronics. It is also conceivable to depict the measured density values not over the area, but rather along a lane of travel, that is, along a line.

Contactless density sensors 4-2, which acquire a measurement signal without touching the material, may be mounted at a suitable place on the tractor according to the depiction in the drawing and necessitate no separate device for making contact with the agricultural material 2.

It is also possible to use density sensors 4 that, in addition to the density, measure the moisture. However, it is also possible for a moisture sensor 9 to be used as a separate independent sensor. This moisture sensor 9 can measure the moisture of the agricultural material 2 with and without contact to the surface.

Furthermore, the evaluating unit 5 may be provided with a memory storage device for recording the measured data. This makes possible a comparison of the acquired data with earlier measurements.

Fodder silos are emptied after about one year. Therefore, the data may be read out and stored externally, so that it is possible at any time to obtain an overview of the condition in the silos.

The device 3 may be employed on all compacting vehicles or machinery with which agricultural materials 2 are compacted on open surfaces, in halls, or in horizontal silos for conservation, including tractors, wheeled loaders, vibrating rollers, or the like. A use of the process or of the device 3 of the invention for compacting other substances or subsurfaces is equally conceivable.

Figure 2:
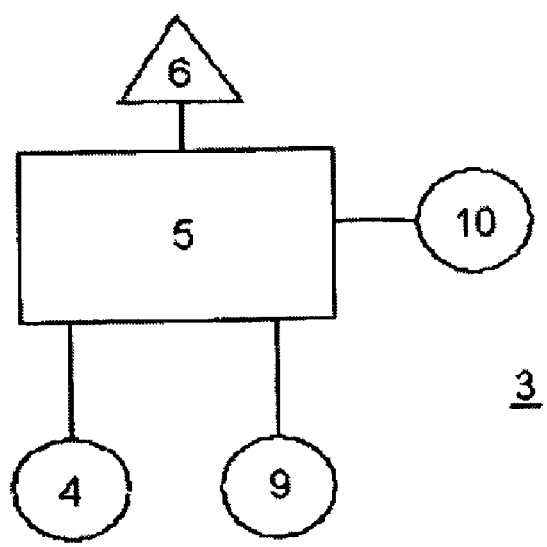
FIG. 2 a schematic depiction of the device.

FIG. 2 shows a device 3 by means of which, through a density sensor 4, the density of an agricultural material 2 can be measured. In addition to the density, it is possible by using the moisture sensor 9 to determine the moisture of the agricultural material 2. The values measured by the density sensor 4 and the moisture sensor 9 are conveyed to an evaluating unit 5. In addition, it is also possible to determine the position by way of a navigation system 10. The positional data determined by the navigation system 10 are likewise conveyed to the evaluating unit 5.

In the evaluating unit 5, the measured values are compared with the specific specified values for the existing agricultural material 2. The evaluating unit 5 conveys the data to a display unit 6. With the display unit 6, the acquired data can be visualized on a monitor or indicated by acoustical signals.

Radiometric processes with gamma absorption or gamma scatter arrangements may be used for density determination. Gamma back-scatter probes are single-rod probes 11, in which the radioactive radiation source and the detector are arranged inside of a tube. Between the radioactive radiation source and the detector is situated an absorber having the highest density possible, which shields the detector against direct radiation. The principle of measurement of the gamma back-scatter probe is based on the interaction of the gamma quanta with the surrounding material. The number of gamma quanta registered by the detector is obtained as a function of the density of the material to be measured and passes through a maximum. The position of the maximum, the measured volume, the measurement range, and the sensitivity depend on the source-detector arrangement as well as the choice of radioactive radiation source (energy).

Figure 3:
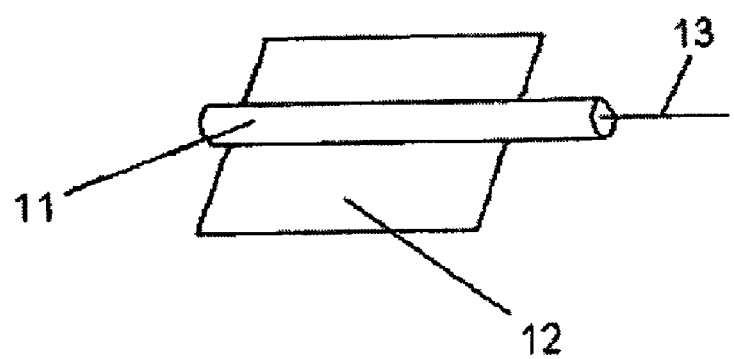
FIG. 3 a sketch of the measuring probe on a plate.

FIG. 3 shows a single-rod probe 11 (measuring tube), which is attached to a plate 12, by means of which the measuring probe 18 lies on the silo surface, for use in the silo. The single-rod probe 11 is connected here to the evaluating unit 5 through a connecting cable 13. Cesium 137 with an activity of 75 MBq is used as the source. The measuring tube can also be installed in a runner.

In order to be able to prevent damage to the measuring probe 18, the measuring probe 18 can also be guided in a runner 14 over the agricultural material 2.

Figure 4:
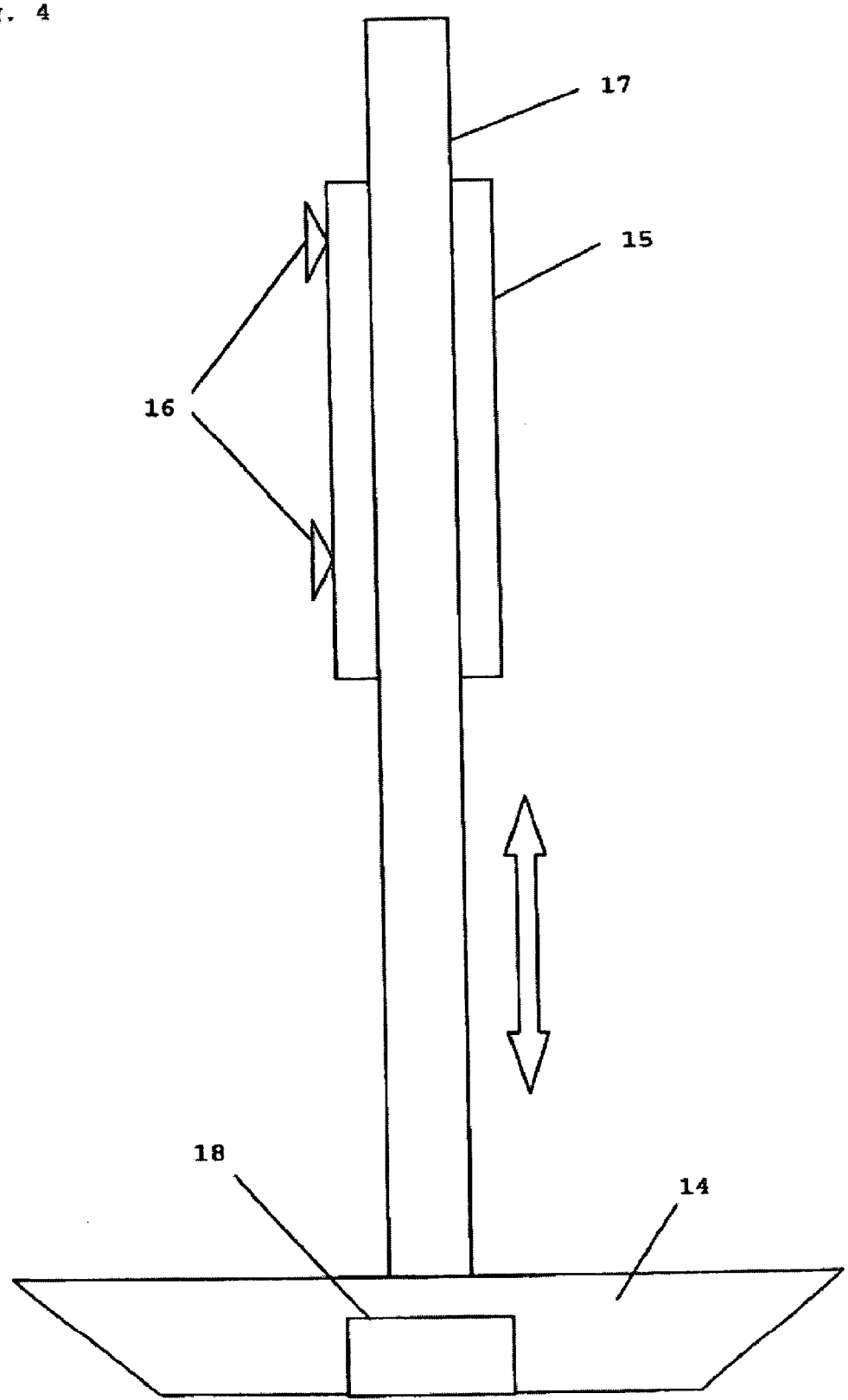
FIG. 4 a schematic depiction of a runner.

FIG. 4 shows a schematic depiction of a runner 14 in which the measuring probe 18 is accommodated. The distance of the runner 14 from the agricultural material 2 can be varied. To this end, the runner 14 has a linear guide with a guide shaft 17, which is gripped in a guide 15. The guide shaft 17 can move in the guide 15. Moreover, attached to the guide 15 is a fastener 16, with which the device can be fixed in place on a compacting apparatus 1.

Figure 5:
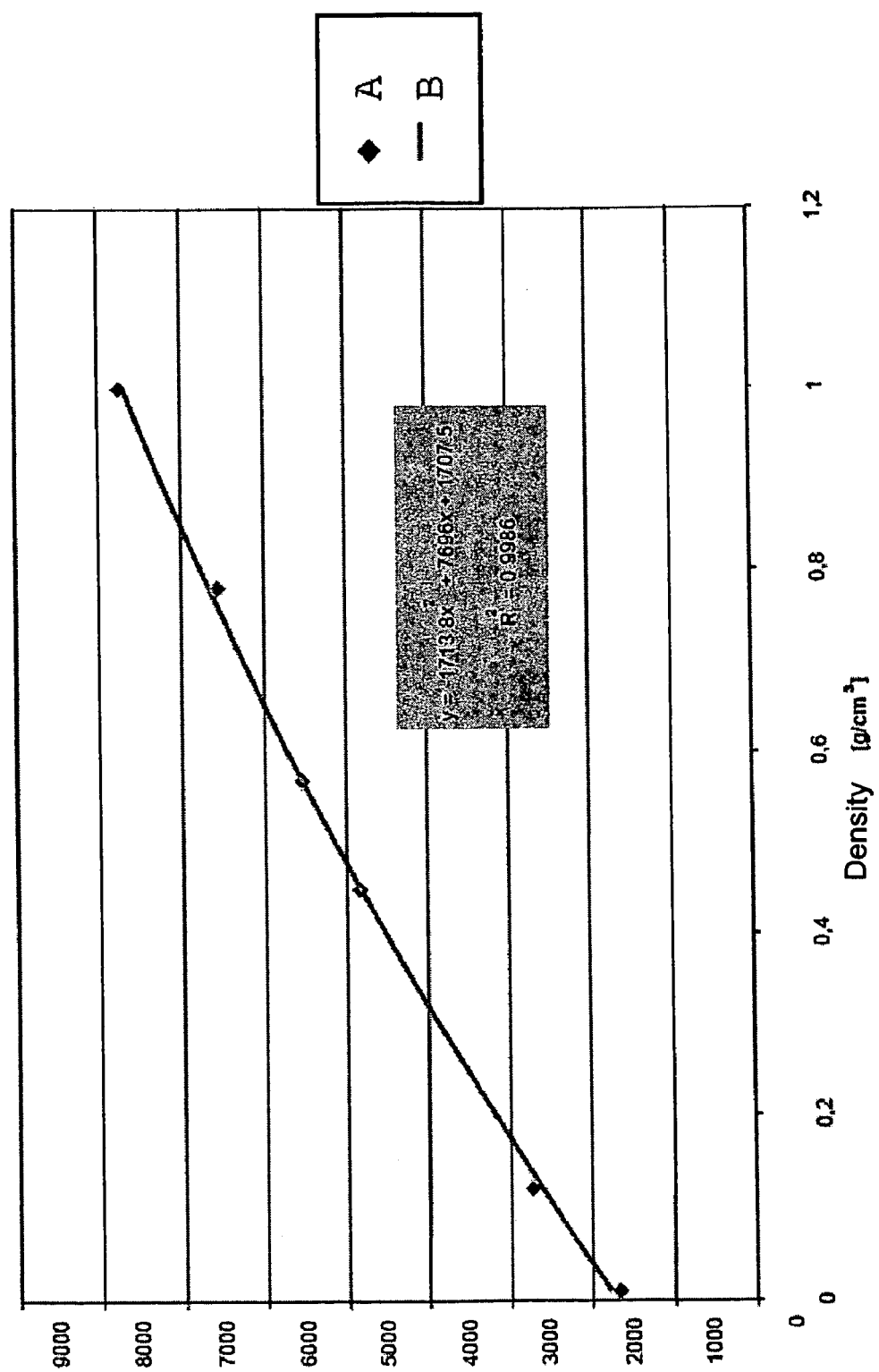
FIG. 5 a diagram of the calibration of a radiometric probe.

FIG. 5 shoes a diagram of the calibration of a radiometric rod probe having a plate 12 (A=pulse rate min$^{-1}$, B=polynomial pulse rate min$^{-1}$). Cesium 137 with an activity of 75 MBq was used as the source.

Figure 6:
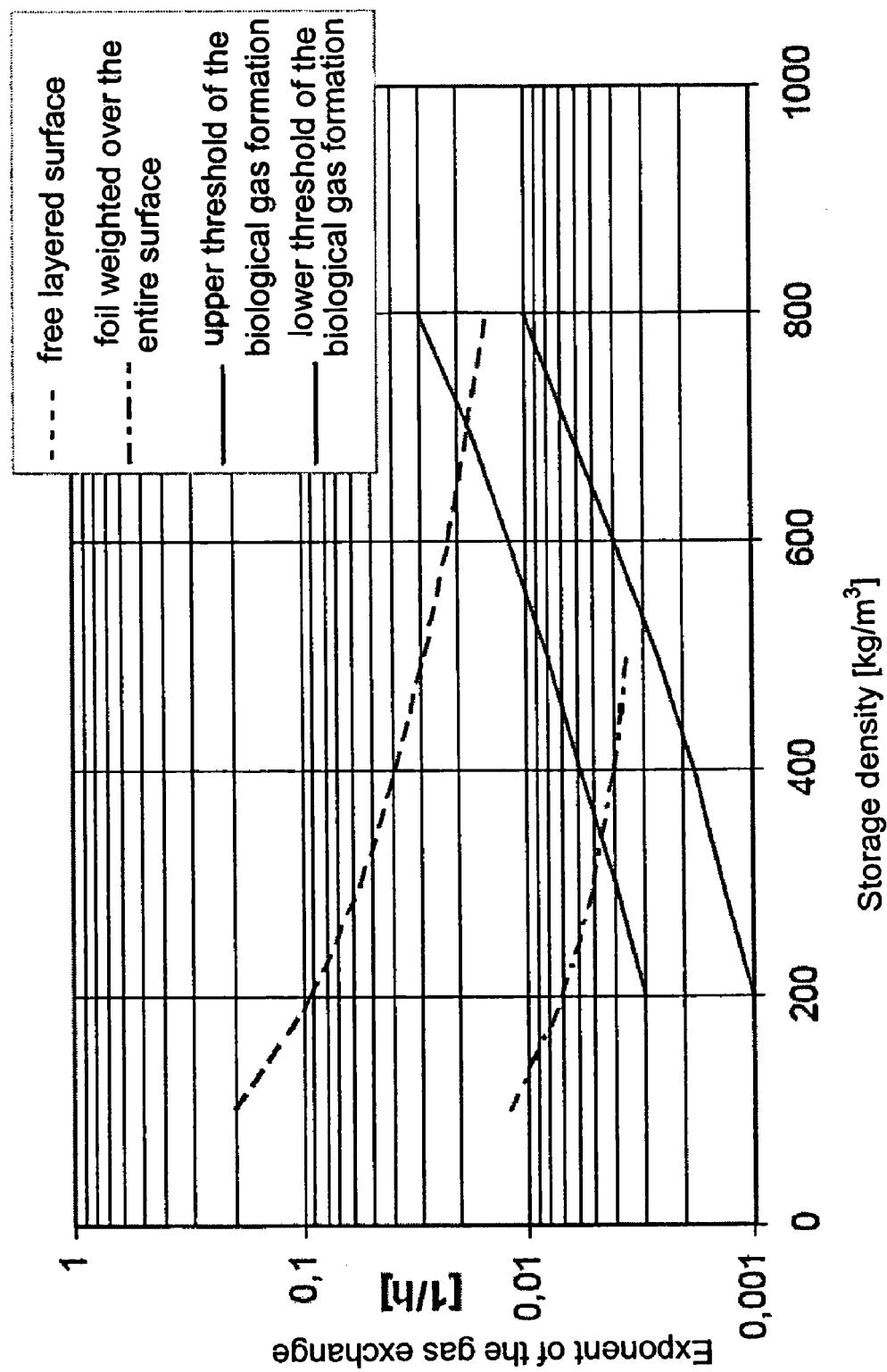
FIG. 6 a diagram of the gas exchange.

Shown in FIG. 6 is a diagram in which the exponent of the gas exchange and the gas formation are plotted as a function of the storage density of the original substance of the silo-stored material for an open-silo material surface and for a surface covered with a foil.

The density of the silo-stored material has quite a substantial influence on the success of silo storage. For low densities, the pore fraction in the agricultural material 2 is higher. This promotes gas exchange and heat evolution. Regarded as criterion for the magnitude of the storage density of the original substance is that the gas exchange may not be greater than the gas formation in the silo-stored material. This means that, for withered silo-stored material, without covering the open silo-stored material surface, a density of >750 kg OS/m$^3$ must be present (OS=original substance). Because this cannot be achieved in practice, the outside air is excluded by covering with foil. For foil weighted over its entire surface, a storage density of only 400-500 kg OS/m$^3$ is necessary (see FIG. 6).

The requirements placed on the storage density of chopped grass as a function of the dry mass content (DM) for a gas exchange of 20 L/m$^2$h is presented in the following table.

| Dry mass content (in %) | Dry mass density (in kg DM/m$^3$) |
|---|---|
| 30 | 200 |
| 40 | 230 |
| 50 | 250 |

The storage densities depend, above all, on the effective static pressures and on the physical characteristics of the silo-stored material. The dry mass content (DM), the flexural strength of the leaves and stalks, and the chopped length have a decisive influence.

LIST OF REFERENCE NUMBERS

1 compacting apparatus
2 (agricultural) material
3 device
4 density sensor
4-1 density sensor (with contact to ground)
4-2 contactless density sensor (without contact to ground)
5 evaluating unit
6 display unit
7 measuring wheel
8 antenna of the navigation system
9 moisture sensor
10 navigation system
11 single-rod probe
12 plate
13 connecting cable
14 runner
15 guide
16 fastener to the tractor
17 guide shaft
18 measuring probe

The invention claimed is:

1. A process for measuring the mechanical compaction in the depth of a previously harvested agricultural material, said process comprising the steps of:

mechanically compacting a previously harvested agricultural material, wherein said mechanical compacting step is performed by driving over the previously harvested agricultural material; and measuring the density of the compacted agricultural material continuously or discontinuously;

wherein said mechanically compacting and measuring steps are conducted at the same time during the ongoing compaction of the agricultural material.

2. The process according to claim 1, further characterized in that said measuring is performed with a density sensor and in that the measured data of the density sensor are conveyed to an evaluating unit and displayed on a display unit.

3. The process according to claim 2, further characterized in that the values measured by the density sensor are compared with a specified value of the agricultural material in the evaluating unit and the deviation between the values is conveyed to the display unit.

4. The process according to claim 2, further characterized in that measurement with another sensor is made of the moisture of the agricultural material and the measured values of the moisture determination are conveyed to the evaluating unit.

5. The process according claim 4, further characterized in that, in the evaluating unit, the measured values are compared with a specified value of the agricultural material, taking into consideration the moisture of the agricultural material, and the deviation is conveyed to the display unit.

6. The process according to claim 2, further characterized in that the position at which a measured value is recorded is determined and this positional value is conveyed to the evaluating unit.

7. The process according to claim 2, further characterized in that the display unit indicates the density of the agricultural material acoustically and/or displays it visually.

8. The process according to claim 1, further characterized in that the density at the surface of the agricultural material is measured.

9. A device for carrying out the process according to claim 1, consisting of at least one measuring sensor and at least one display unit, which are connected to an evaluating unit.

10. The device according to claim 9, further characterized in that the measuring sensor is a density sensor and a moisture sensor.

11. The device according to claim 9, further characterized in that the measuring sensor is fastened to a plate.

12. The device according to claim 9, further characterized in that a measuring unit is provided for the determination of the position of the measurement.

13. The device according to claim 12, further characterized in that the measuring unit is a navigation system, which determines the position of the measurement and conveys it to the evaluating unit.

14. The device according to claim 12, further characterized in that the measuring unit is a path measurement system, a distance measurement system, or a position measurement system.

15. The device according to claim 14, further characterized in that two or more of the measurement systems mentioned are provided.

16. The device according to claim 9, further characterized in that the values measured by the measuring sensor and/or the measuring unit and compared with the specified value of the agricultural material by the evaluating unit are indicated acoustically by a display unit and/or are displayed acoustically.

17. The device according to claim 9, further characterized in that it is installed in a compacting apparatus or is fastened to it.

18. The device according to claim 17, further characterized in that individual parts of the device are attached to the compacting apparatus, while the remaining parts of the compacting apparatus are arranged in a stationary measuring station.

19. The device according to claim 9, further characterized in that the device is fastened to a separate measuring vehicle.

20. The device according to claim 9, further characterized in that the device or parts of the device are arranged on a runner.

21. A process for measuring the mechanical compaction in the depth of a harvested agricultural material, said process comprising the steps of:
  (a) providing a quantity of harvested agricultural material;
  (b) mechanically compacting the harvested agricultural material, wherein said mechanical compacting step is performed by driving over the harvested agricultural material;
  (c) measuring the density of the harvested agricultural material mechanically compacted in step (b); and
  (d) repeating steps (b) and (c) at least once with respect to the harvested agricultural material mechanically compacted in step (b).

22. The process as claimed in claim 21 wherein said mechanically compacting step is performed inside a silo.

* * * * *